United States Patent
Yamamoto et al.

[11] 3,933,824
[45] Jan. 20, 1976

[54] PIPERAZINOBUTYROPHENONE DERIVATIVES

[75] Inventors: Hisao Yamamoto, Nishinomiya; Masaru Nakao; Kikuo Sasajima, both of Toyonaka; Isamu Maruyama, Minoo; Shigenari Katayama, Takarazuka, all of Japan

[73] Assignee: Sumitomo Chemical Company, Limited, Osaka, Japan

[22] Filed: Jan. 22, 1973

[21] Appl. No.: 325,372

Related U.S. Application Data

[63] Continuation-in-part of Ser. No. 119,426, Feb. 26, 1971, abandoned.

[30] Foreign Application Priority Data

Mar. 6, 1970 Japan.............................. 45-19458
May 14, 1970 Japan.............................. 45-41495

[52] U.S. Cl. 260/268 PH; 260/240 G; 260/268 BC; 260/268 R; 424/250
[51] Int. Cl.² ........................................ C07D 295/12
[58] Field of Search................... 260/268 R, 268 PH

[56] References Cited
UNITED STATES PATENTS

| | | | |
|---|---|---|---|
| 2,997,472 | 8/1961 | Janssen......................... | 260/268 PH |
| 3,538,091 | 11/1970 | de Stevens..................... | 260/268 PH |
| 3,562,277 | 2/1971 | Hansen et al.................. | 260/268 PH |
| 3,637,704 | 1/1972 | Umemoto et al............. | 260/268 PH |
| 3,658,821 | 4/1972 | Fauran et al. ................ | 260/268 PH |

FOREIGN PATENTS OR APPLICATIONS 996,702  6/1965  United Kingdom

Primary Examiner—Richard J. Gallagher
Assistant Examiner—Jose Tovar
Attorney, Agent, or Firm—Stevens, Davis, Miller & Mosher

[57] ABSTRACT

Central nervous system active butyrophenone derivatives in which γ-piperazinobutyrophenone derivatives of the formula,

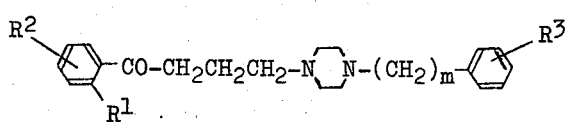

wherein $R^1$ is hydrogen, amino, $C_1$–$C_5$ alkanoylamino, $C_1$–$C_4$ alkylamino or N-($C_1$–$C_4$ alkyl)($C_1$–$C_5$ alkanoyl) amino; $R^2$ is hydrogen or halogen; $R^3$ is hydrogen, halogen, $C_1$–$C_4$ alkyl, $C_1$–$C_4$ alkoxy or trifluoromethyl; and $m$ is 0, 1 or 2, and acid addition salts thereof, can be prepared by reacting an indole derivative of the formula,

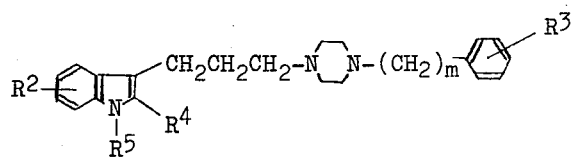

wherein $R^2$, $R^3$ and $m$ are the same as defined above, and $R^4$ and $R^5$ are hydrogen or $C_1$–$C_4$ alkyl respectively, with an oxidizing agent to yield an o-alkanoylamino-γ-piperazinobutyrophenone derivative of the formula,

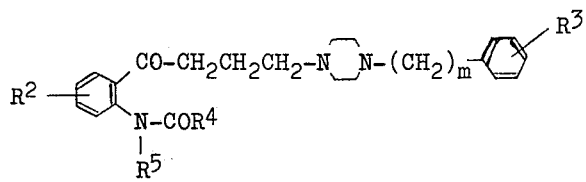

wherein $R^2$, $R^3$, $R^4$, $R^5$ and $m$ are the same as defined above, and further, if necessary, hydrolyzing the product to yield an o-amino-γ-piperazinobutyrophenone derivative of the formula,

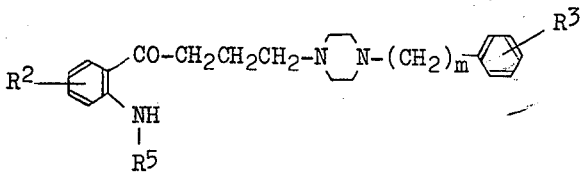

wherein $R^2$, $R^3$, $R^5$ and $m$ are the same as defined above, and further diazotizing, if desired, in case $R^5$ is hydrogen, the obtained o-amino-γ-piperazinobutyrophenone derivative and subsequently decomposing the resultant diazonium compound to replace the diazonium group by hydrogen. Among the butyrophenone derivatives thus obtained, those in which $R^1$ is amino, alkanoylamino, alkylamino or N-alkylalkanoylamino and those in which $R^1$ is hydrogen and $R^2$ is halogen substituted at meta-position to carbonyl group are novel compounds.

2 Claims, No Drawings

PIPERAZINOBUTYROPHENONE DERIVATIVES

CROSS REFERENCE TO RELATED APPLICATIONS

This is a continuation-in-part of co-pending application Ser. No. 119,426 filed on Feb. 26, 1971, now abandoned.

The present invention relates to a novel process for producing butyrophenone derivatives. More particularly, the invention relates to a novel process for producing central nervous system active γ-piperazinobutyrophenone derivatives. The invention also pertains to novel central nervous system active γ-piperazinobutyrophenone derivatives and pharmaceutical use of the same.

The present inventors studied in order to find an advantageous process in which a substituted γ-piperazinobutyrophenone derivative having a substituent at the ortho position can be produced. As a result, the present inventors found a novel and advantageous process for producing various substituted γ-piperazinobutyrophenone derivatives including such ortho-substituted compounds. The most important characteristic of the process of our finding resides in the production of o-alkanoylamino-γ-piperazinobutyrophenone derivatives by the oxidation of 3-(γ-piperazinopropyl)indole derivatives. The alkanoylamino group of the thus-obtained o-alkanoylamino-γ-piperazinobutyrophenone derivatives can be converted to unsubstituted or substituted amino group by an ordinary hydrolysis reaction and further subsequently to hydrogen by an ordinary diazotization and decomposition. Therefore, according to the process of our finding, various γ-piperazinobutyrophenone derivatives can be produced very advantageously.

Accordingly, an object of the present invention is to provide a novel and advantageous process for producing γ-piperazinobutyrophenone derivatives.

Another object of the invention is to provide novel central nervous system active γ-piperazinobutyrophenone derivatives.

A further object of the invention is to provide a pharmaceutical use of such γ-piperazinobutyrophenone derivatives.

Other objects and merits of the invention will be apparent from the following description.

In order to accomplish these objects, the present invention provides a process for producing a γ-piperazinobutyrophenone compound of the formula,

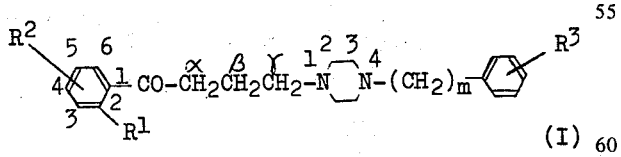

(I)

wherein $R^1$ is hydrogen, amino, $C_1$–$C_5$ alkanoylamino, ($C_1$–$C_4$ alkyl)amino or N-($C_1$–$C_4$ alkyl) ($C_1$–$C_5$ alkanoyl) amino; $R^2$ is hydrogen or halogen; $R^3$ is hydrogen, halogen, $C_1$–$C_4$ alkyl, $C_1$–$C_4$ alkoxy or trifluoromethyl; and $m$ is 0, 1 or 2; and an acid addition salt thereof, which comprises contacting an indole compound of the formula,

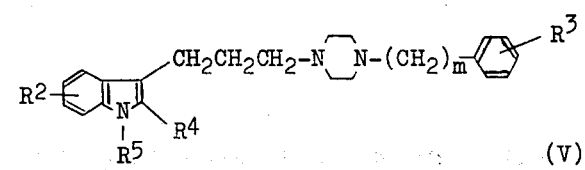

(V)

wherein $R^4$ and $R^5$ are hydrogen or $C_1$–$C_4$ alkyl respectively, and $R^2$, $R^3$ and $m$ are the same as defined above, with an oxidizing agent to yield a compound of the formula,

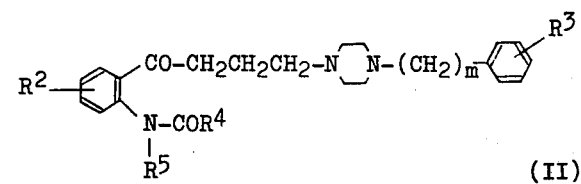

(II)

wherein $R^2$, $R^3$, $R^4$, $R^5$ and $m$ are the same as defined above, and if necessary, hydrolyzing the resulting compound of the formula (II) to a compound of the formula,

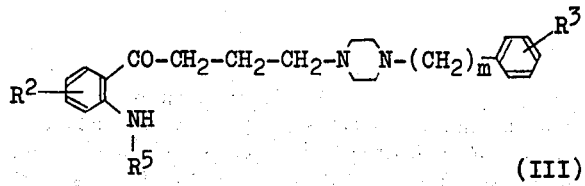

(III)

wherein $R^2$, $R^3$, $R^5$ and $m$ are the same as defined above, and further diazotizing, if desired, in case $R^5$ is hydrogen, the resulting compound of the formula (III) and subsequently decomposing the resulting diazonium compound to replace the diazonium group by hydrogen to yield a compound of the formula,

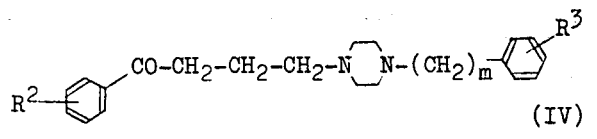

(IV)

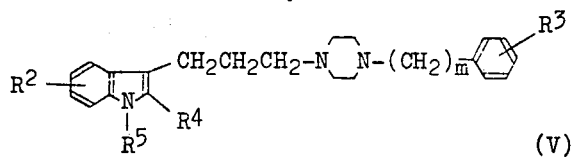

(V)

wherein R², R³ and m are the same as defined above.

Further, the present invention provides a novel compound of the formulas,

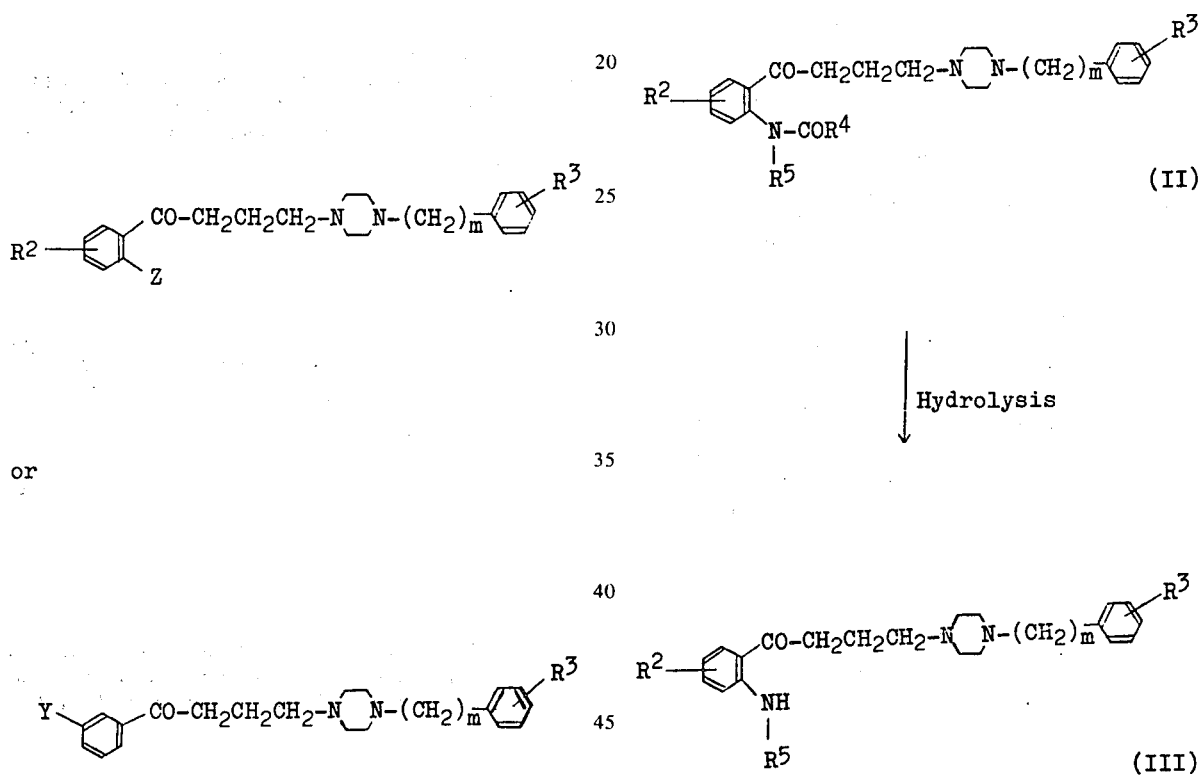

(II)

Hydrolysis (III)

or

Diazotization and decomposition wherein Z is amino, $C_1$–$C_4$ alkylamino, $C_1$–$C_5$ alkanoylamino or N-($C_1$–$C_4$ alkyl) ($C_1$–$C_5$ alkanoyl)amino; R³ is hydrogen, halogen, $C_1$–$C_4$ alkyl, $C_1$–$C_4$ alkoxy, or trifluoromethyl; m is 0, 1 or 2; R² is hydrogen or halogen; and Y is halogen; and a pharmaceutically acceptable acid addition salt thereof.

Furthermore, the present invention provides a pharmaceutical composition containing a novel compound as defined above as active ingredient.

In the present invention, examples of halogen include fluorine, chlorine, bromine or iodine atom.

These compounds of the present invention of the formula (I) above may be prepared by a process as shown by the following reaction scheme:

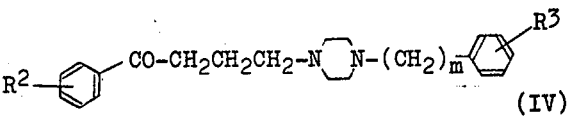

(IV)

wherein $R^2$, $R^3$, $R^4$, $R^5$ and $m$ have the same meanings as defined above.

The 3-(γ-piperazinopropyl)indole compounds of the formula (V), starting materials in the present invention, are easily prepared by reducing the corresponding amide derivatives of the formula (VI),

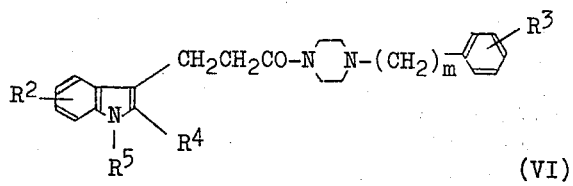

(VI)

wherein $R^2$, $R^3$, $R^4$, $R^5$ and $m$ have the meanings given above. A reducing agent such as alkali metal in alcoholic solvent, hydrogen in the presence of a catalyst, metal hydride and the like can be preferably employed. An electrolytic reduction procedure can also be used for the purpose. It is especially preferable to use a metal hydride as a reducing agent such as lithium aluminum hydride, diisobutyl aluminum hydride, boron hydride or the like, in an inert organic solvent such as, for example, ether, tetrahydrofuran, dioxane, N-ethylmorpholine and the like.

The present compounds of the formula (V) can also be prepared by the Grignard reaction of an indole derivative (VII) represented by the following equation;

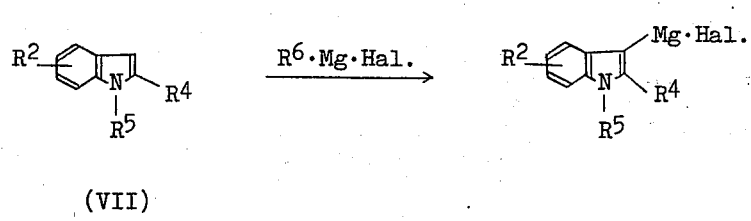

(VII)

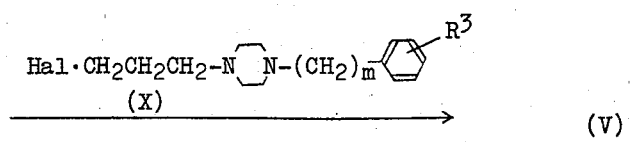

(V)

wherein $R^6$ is lower alkyl, Hal. is halogen and $R^2$, $R^3$, $R^4$, $R^5$ and $m$ have the meanings given above. The above-represented indole Grignard reagent can be prepared by a method well known to the art and the Grignard reaction of the next process is preferably carried out at a temperature between −10° and 40°C in an inert organic solvent such as, for example, ether, tetrahydrofuran, dioxane, anisole, benzene, toluene, xylene or the like.

By the above-mentioned procedure, the 3-(γ-piperazinopropyl)indole compounds of the formula (V) can readily be prepared, examples of which are as follows:

3-[γ-(4-Phenylpiperazino)propyl]indole
2-Methyl-3-[γ-(4-phenylpiperazino)propyl]indole
3-[γ-(4-o-Methoxyphenylpiperazino)propyl]indole
2-Methyl-3-[γ-(4-o-methoxyphenylpiperazino)-propyl]-indole
3-[γ-(4-o-Tolypiperazino)propyl]indole
3-[γ-(4-o-Chlorophenylpiperazino)propyl]indole
1,2-Dimethyl-3-[γ-(4-phenylpiperazino)propyl]indole
2-Methyl-3-[γ-(4-phenylpiperazino)propyl]-5-fluoroindole
2-Methyl-3-[γ-(4-phenylpiperazino)propyl]-6-fluoroindole
2-Methyl-3-[γ-(4-o-methoxyphenylpiperazino)-propyl]-6-fluoroindole
1,2-Dimethyl-3-[γ-(4-o-methoxyphenylpiperazino)-propyl]-6-fluoroindole
1-Ethyl-3-[γ-(4-o-methoxyphenylpiperazino)-propyl]-6-fluoroindole
2-Methyl-3-[γ-(4-m-trifluoromethylphenyl-piperazino)-propyl]-5-fluoroindole
2-Methyl-3-[γ-(4-p-fluorophenylpiperazino)propyl]-6-fluoroindole
2-Methyl-3-[γ-(4-phenylpiperazino)propyl]-6-chloroindole
2-Methyl-3-[γ-(4-o-methoxyphenylpiperazino)-propyl]-6-chloroindole
2-Methyl-3-[γ-(4-o-chlorophenylpiperazino)-propyl]-6-chloroindole
3-[γ-(4-Benzylpiperazino)propyl]indole
2-Methyl-3-[γ-(4-benzylpiperazino)propyl]indole
2-Methyl-3-[γ-(4-benzylpiperazino)propyl]-5-fluoroindole
2-Methyl-3-[γ-(4-benzylpiperazino)propyl]-6-fluoroindole
2-Methyl-3-[γ-(4-p-chlorobenzylpiperazino)propyl]-6-fluoroindole
2-Methyl-3-[γ-(4-o-methoxybenzylpiperazino)-propyl]-6-fluoroindole
2-Methyl-3-[γ-(4-phenethylpiperazino)propyl]-6-fluoroindole
2-Methyl-3-[γ-(4-o-methoxyphenethylpiperazino)-propyl]-6-fluoroindole
2-Methyl-3-[γ-(4-m-methoxyphenethylpiperazino)-propyl]-6-fluoroindole
2-Methyl-3-[γ-(4-p-chlorophenethylpiperazino)-propyl]-6-fluoroindole The 1-[β-(3-indolyl)propionyl]piperazine compounds of the formula (VI), which are used as an intermediate compound in the present invention, can be

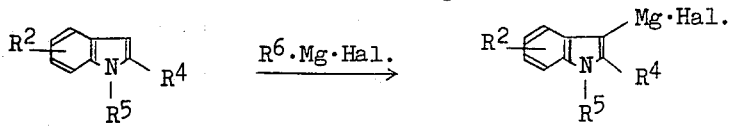

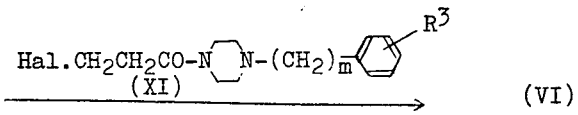

(VII)

prepared by a variety of several methods, for example, by reacting an indolylpropionic acid of the formula (VIII) or its functionally active derivative with a piperazine of the formula (XII). The reaction is represented by the equation;

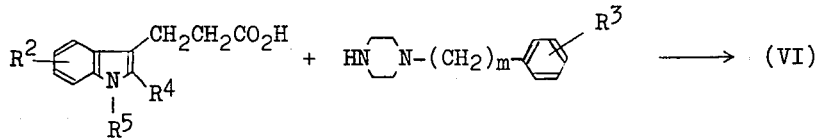

wherein $R^2$, $R^3$, $R^4$, $R^5$ and $m$ have the meanings given above. The said functionally active derivatives are, for example, acid chloride, acid bromide, acid anhydride, mixed acid anhydride, p-nitrophenyl ester and the like, and the mixed acid anhydride mentioned above includes those prepared by treating with ethyl chloroformate, isobutyl chloroformate or the like. The reaction is preferably carried out in the presence of a basic agent or a condensing agent such as pyridine, triethylamine, sodium carbonate, sodium hydroxide, dicyclohexylcarbodiimide and the like in a suitable inert organic solvent such as tetrahydrofuran, ether, dioxane, benzene, toluene, chloroform, dimethylformamide and the like.

Another procedure for producing the present compound of the formula (VI) is a one-step cyclization reaction of a phenylhydrazone compound of the formula (IX),

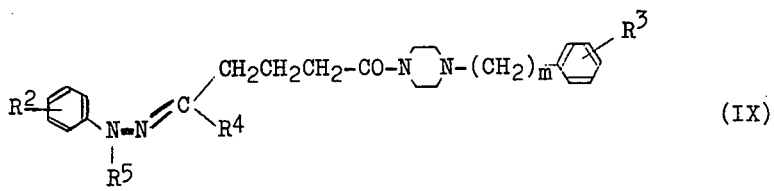

wherein $R^2$, $R^3$, $R^4$, $R^5$ and $m$ have the meanings given above. The reeaction is carried out by heating the phenylhydrazone preferably in the presence of an acid condensing agent such as, for example, hydrogen choride, sulfuric acid, phosphoric acid, glacial acetic acid, p-toluenesulfonic acid, zinc chloride, copper chloride, boron fluoride, polyphosphoric acid and the like, and in a suitable solvent such as methanol, ethanol, isopropanol, benzene, toluene, acetic acid, water and the like.

The present intermediate compounds of the formula (VI) can also be prepared by the Grignard reaction of an indole compound of the formula (VII) represented by the following equation;

wherein $R^2$, $R^3$, $R^4$, $R^5$, $R^6$, Hal. and $m$ have the same meanings as defined above. The Grignard reaction is preferably carried out at a temperature between 0° and 150°C and in the absence or presence of an inert organic solvent such as ether, tetrahydrofuran, dioxane, anisole, benzene, toluene, xylene or the like.

By the above-mentioned procedure, the 1-[β-(3-indolyl)propionyl]piperazine derivatives of the formula (VI) are readily prepared, examples of which are as follows:

1-[β-(3-Indolyl)propionyl]-4-phenylpiperazine
1-[β-(2-Methyl-3-indolyl)propionyl]-4-phenylpiperazine
1-[β-(2-Methyl-3-indolyl)propionyl]-4-(o-methoxyphenyl)piperazine
1-[β-(2-Methyl-5-fluoro-3-indolyl)propionyl]-4-phenylpiperazine
1-[β-(2-Methyl-6-fluoro-3-indolyl)propionyl]-4-phenylpiperazine
1-[β-(2-Methyl-6-fluoro-3-indolyl)propionyl]-4-(o-methoxyphenyl)piperazine
1-[β-(2-Methyl-6-fluoro-3-indolyl)propionyl]-4-(p-fluorophenyl)piperazine
1-[β-(2-Methyl-6-chloro-3-indolyl)propionyl]-4-(p-methoxyphenyl)piperazine
1-[β-(2-Methyl-6-chloro-3-indolyl)propionyl]-4-(o-chlorophenyl)piperazine
1-[β-(3-Indolyl)propionyl]-4-benzylpiperazine
1-[β-(2-Methyl-5-fluoro-3-indolyl)propionyl]-4-benzylpiperazine
1-[β-(2-Methyl-6-fluoro-3-indolyl)propionyl]-4-benzylpiperazine
1-[β-(2-Methyl-6-fluoro-3-indolyl)propionyl]-4-(p-methoxybenzyl)piperazine
1-[β-(2-Methyl-6-fluoro-3-indolyl)propionyl]-4-phenethylpiperazine 1-[β-(2-Methyl-6-fluoro-3-indolyl)propionyl]-4-(p-methoxyphenethyl)piperazine γ-Piperazinobutyrophenones of the formula (II) can be prepared by contacting the above-obtained 3-(γ-piperazinopropyl)indoles of the formula (V) with an oxidizing agent. In the oxidative cleavage reaction it is preferred to use an oxidizing agent such as ozone, hydrogen peroxide, performic acid, peracetic acid, perbenzoic acid, chromic acid or potassium permanganate, although the oxidizing agent of the present invention is not limited to the exemplified ones and others may be used.

Generally, the reaction proceeds readily at room temperature, but the temperature may be higher or lower if necessary to effect the desired control of the reaction. The oxidizing agent is preferably chromic acid or ozone. The reaction is preferably effected in the presence of a solvent. The choice of solvent depends on the oxidizing agent employed, and the solvent is selected from the group consisting of water, acetone, carbon tetrachloride, acetic acid, sulfuric acid and the like. The oxidizing agent is used in the stoichiometric amount or more. The reaction temperature varies depending on the oxidizing agent employed.

When the oxidation is carried out by use of chromic acid in the presence of acetic acid, it is preferable that the chromic acid may be used in 2–3 times the equimolar amount and that the reaction may be carried out at room temperature. A 3-(γ-piperazinopropyl)-indole derivative is dissolved or suspended in the solvent and the oxidizing agent is added to the solution or suspension with stirring. Generally, the reaction terminates within about 24 hours.

When the oxidation is carried out by use of ozone, the reaction is preferably carried out at room temperature. A 3-(γ-piperazinopropyl)indole derivative is dissolved or suspended in a solvent such as formic acid, acetic acid, carbon tetrachloride or the like and ozonized oxygen is bubbled into the solution or suspension with stirring.

The desired γ-piperazinobutyrophenone derivative can be separated from the reaction mixture in a crude form by extraction, with or without prior neutralization, and by evaporation to dryness. The product is further purified, if desired, by recrystallization from a suitable solvent such as ethanol, isopropanol or the like in a standard manner.

The resulting compound of the formula (II) can be hydrolyzed to give a corresponding deacylated compound of the formula (III). The hydrolysis is accomplished under an acidic or alkaline condition according to an ordinary hydrolysis procedure.

γ-Piperazinobutyrophenones of the formula (IV) are prepared by diazotization of the above-obtained o-amino-compound of the formula (III) wherein $R^5$ is hydrogen, and subsequent treatment of the resulting diazonium salt with a suitable agent to replace the diazonium group by hydrogen.

The diazotization is performed by a conventional method and the replacement reaction is conducted as follows:

By treating the diazonium salt with a reducing agent such as ethanol, hypophosphorous acid, alkaline formaldehyde, sodium stannite and the like, there can be obtained γ-piperazinobutyrophenones of the formula (IV)

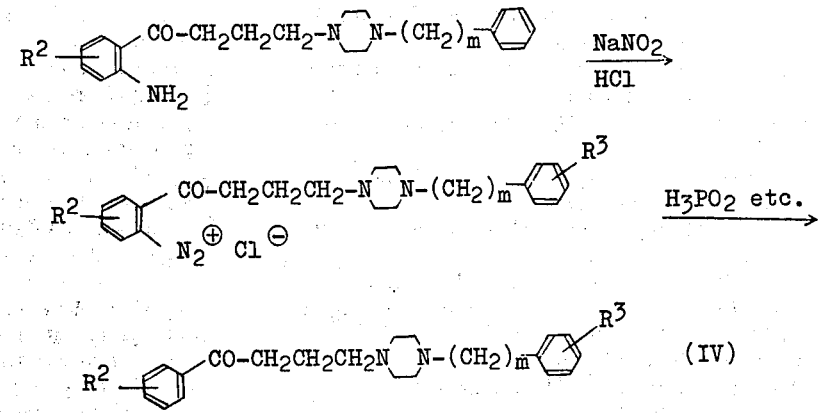

($R^2$, $R^3$ and $m$ have the same meanings as described above.)

By the above-mentioned procedure, the γ-piperazinobutyrophenone derivatives (I) are easily prepared, examples of which are as follows:

γ-(4-Phenylpiperazino)-2-acetylaminobutyrophenone

γ-(4-Phenylpiperazino)-2-acetylamino-5-fluorobutyrophenone

γ-(4-Phenylpiperazino)-2-acetylamino-4-fluorobutyrophenone

γ-(4-Phenylpiperazino)-2-N-(methyl)acetylamino-4-fluorobutyrophenone

γ-[4-(o-Methoxyphenyl)piperazino]-2-acetylamino-4-fluorobutyrophenone

γ-[4-(o-Methoxyphenyl)piperazino]-2-acetylamino-5-fluorobutyrophenone

γ-(4-Phenylpiperazino)-2-acetylamino-4-chlorobutyrophenone

γ-(4-Benzylpiperazino)-2-acetylamino-4-fluorobutyrophenone

γ-[4-(p-Methoxybenzyl)piperazino]-2-acetylamino-4-fluorobutyrophenone

γ-[4-(p-Fluorobenzyl)piperazino]-2-acetylamino-4-fluorobutyrophenone

γ-[4-(p-Methylbenzyl)piperazino]-2-acetylamino-4-fluorobutyrophenone

γ-[4-(m-Chlorobenzyl)piperazino]-2-acetylamino-4-fluorobutyrophenone

γ-(4-Phenethylpiperazino)-2-acetylamino-4-fluorobutyrophenone

γ-(4-Phenylpiperazino)-2-aminobutyrophenone

γ-(4-Phenylpiperazino)-2-amino-5-fluorobutyrophenone

γ-(4-Phenylpiperazino)-2-amino-4-fluorobutyrophenone

γ-(4-Phenylpiperazino0-2-methylamino-4-fluorobutyrophenone
γ-[4-(o-Methoxyphenyl)piperazino]-2-amino-4-fluorobutyrophenone
γ-[4-(o-Methoxyphenyl)piperazino]-2-ethylamino-4-fluorobutyrophenone
γ-[4-(p-Tolyl)piperazino]-2-amino-4-fluorobutyrophenone
γ-[4-(o-Methoxyphenyl)piperazino]-2-amino-5-fluorobutyrophenone
γ-(4-Phenylpiperazino)-2-amino-4-chlorobutyrophenone
γ-[4-(o-Chlorophenyl)piperazino]-2-amino14-chlorobutyrophenone
γ-(4-Benzylpiperazino)-2-amino-4-fluorobutyrophenone
γ-[4-(m-Chlorobenzyl)piperazino]-2-amino-4-fluorobutyrophenone
γ-[4-(p-Methoxybenzyl)piperazino]-2-amino-4-fluorobutyrophenone
γ-[4-(p-Fluorobenzyl)piperazino]-2-amino-4-fluorobutyrophenone
γ-[4-(p-Methylbenzyl)piperazino]-2-amino-4-fluorobutyrophenone
γ-[4-(p-Methoxyphenethyl)piperazino]-2-amino-4-fluorobutyrophenone
γ(4-Phenylpiperazino)-3-fluorobutyrophenone
γ-(4-Phenylpiperazino)-4-fluorobutyrophenone
γ-[4-(o-Methoxyphenyl)piperazino]-4-fluorobutyrophenone
γ-[4-(o-Methoxyphenyl)piperazino]-3-fluorobutyrophenone
γ-[4-(o-Chlorophenyl)piperazino]-4-chlorobutyrophenone
γ-[4-(p-Fluorophenyl)piperazino]-4-fluorobutyrophenone
γ-[4-(p-Methoxybenzyl)piperazino]-4-fluorobutyrophenone
γ-[4-o-Methoxybenzyl)piperazino]-4-fluorobutyrophenone
γ-[4-(m-Chlorobenzyl)piperazino]-4-fluorobutyrophenone
γ-[4-(p-Methylbenzyl)piperazino]-4-fluorobutyrophenone
γ-[4-(p-Fluorobenzyl)piperazino]-4-fluorobutyrophenone   γ-[4-(p-Trifluoromethyl-piperazino]-4-fluorobutyrophenone
γ-[4-(p-Methoxyphenethyl)piperazino]-4-fluorobutyrophenone
γ-(4-Phenethylpiperazino)-4-fluorobutyrophenone These compounds can be converted to the corresponding acid addition salts by a procedure known to the art, for example, by dissolving the free base in an aqueous solution containing an appropriate acid and isolating the salt by evaporating the solvent, or by contacting the free base with acid in an organic solvent.

These salts include pharmaceutically acceptable acid addition salts, e.g. hydrochloride, fumarate, formate, acetate, lactate, citrate, sulfonate, maleate, tartrate, methane sulfonate, salicylate and hydrosulfate.

These γ-piperazinobutyrophenone derivatives of the formula (I) and their pharmaceutically acceptable acid addition salts have central nervous system activities and are useful as anti-anxiety, anti-psychotic, anti-emotional, anti-convulsive, anti-psychosis or analgesic drug.

Each of the pharmaceutically active compounds of this invention may be, e.g., incorporated, for oral administration, in a tablet as the sole active ingredient. A typical tablet is constituted by from 1 to 2 per cent binder, e.g. tragacanth; from 3 to 10 per cent lubricant, e.g. talcum; from 0.25–1.0 per cent lubricant, e.g. magnesium stearate; an average dose of active ingredient; and q.s. 100 per cent of filler, e.g. lactose. The usual oral dosage is 1–100 mg per os daily.

The following examples are intended to illustrate the present invention, but not to limit its scope.

EXAMPLE 1

Preparation of the intermediate compound (VI):

a. To a stirred solution of 66.2 g of 2-methyl-5-fluoro-3-indolylpropionic acid and 30.3 g of triethylamine in 400 ml of tetrahydrofuran was added dropwise 32.6 g of ethyl chloroformate at a temperature below 0°C. The stirring was continued for additional 30 minutes below 0°C and thereto was added dropwise a solution of 48.7 g of 4-phenylpiperazine in 100 ml of tetrahydrofuran. After addition was completed, the reaction mixture was stirred for 4 hours at room temperature and then filtered. The filtrate was concentrated under reduced pressure to a residual solid, which was recrystallized from ethanol to give 1-[β-(2-methyl-5-fluoro-3-indolyl)propionyl]-4-phenylpiperazine, melting at 170.0°–171.5°C.

b. To a solution of 10.8 g of phenylhydrazine in 100 ml of 30 % aqueous acetic acid was added 27.4 g of 1-(γ-acetylbutyryl)-4-phenylpiperazine and the resulting mixture was stirred for 30 minutes at room temperature. The precipitate was filtered, and washed with water. The precipitate was added to 180 ml of 5 % ethanolic hydrogen chloride, and the mixture was heated under reflux for 4 hours. The solvent was distilled off under reduced pressure to the residue, to which was added 100 ml of water. The resulting solid substance was recrystallized from ethanol to give 1-[β-(2-methyl-3-indolyl)propionyl]-4-phenylpiperazine, melting at 120°–121°C.

c. 2-methylindole (26.2 g) dissolved in dry ether (100 ml) was added dropwise to the Grignard reagent prepared from 4.9 g of magnesium and 31.2 g of ethyl iodide in 100 ml of dry ether at 20°–25°C and the mixture was gently refluxed until the evolution of ethane ceased. 1-(β-Chloropropionyl)-4-phenylpiperazine (55.6 g) dissolved in dry ether (100 ml) was then slowly added to the resulting reaction mixture at a temperature below 20°C. At first the addition of the latter caused the precipitation of yellowish viscid solid, which finally became cherry-red. After the addition was completed, ether was distilled off under ordinary pressure and the viscid solid mass which remained was heated on a steam bath for 3 hours, and then cooled. The resulting reaction mixture was agitated vigorously with 250 ml of benzene and 200 ml of a 5 % aqueous solution of acetic acid. The benzene layer which was separated was washed with a 10 % aqueous solution of sodium carbonate and water, dried over anhydrous sodium sulfate and concentrated to dryness. The residual solid was recrystallized from ethanol to give 1-[β-(2-methyl-3-indolyl)propionyl]-4-phenylpiperazine, melting at 121°–122°C.

EXAMPLE 2

Preparation of the starting material (V):

a. To a stirred mixture of 21 g of lithium aluminum hydride and 100 ml of dry ether was added dropwise a solution of 67.5 g of 1-[β-(2-methyl-5-fluoro-3- indolyl)propionyl]-4-phenylpiperazine in 900 ml of tetrahydrofuran over a period of 90 minutes under gentle refluxing. Stirring and refluxing were continued for additional 4 hours and to the reaction mixture was added dropwise a mixture of water and tetrahydrofuran under cooling with ice. The resulting precipitate was filtered off and the filtrate was evaporated to dryness. Recrystallization of the residue from benzene gave 2-methyl-3-[γ-(4-phenylpiperazino)propyl]-5-fluoroindole having a melting point of 146.0°–147.0°C.

b. Ethylmagnesium iodide was prepared from 31.9 g of ethyl iodide and 5.0 g of magnesium in 100 ml of dry anisole and the mixture was heated for 1 hour at 50°–60°C. It was then cooled at 10°C, and while a solution of 2-methylindole (13.1 g) in dry anisole (50 ml) was added thereto, the temperature was maintained below 25°C. The mixture was then heated at 50°C until the evolution of ethane ceased. The resulting solution was cooled to −5°C in a cold bath, and a solution of 1-(γ-chloropropyl)-4-phenylpiperazine (52.5 g) in 100 ml of dry benzene was added during 1 hour at a temperature of −5° ± 2°C. The mixture was then stirred for 3 hours at −5°C and allowed to stand in a refrigerator overnight. The mixture was warmed to 20°–25°C for several hours. The precipitate was broken up and the mixture was poured into saturated aqueous ammonium chloride (500 ml) and stirred for 1 hour. The organic layer was separated, and the aqueous layer was extracted with ethyl acetate. The organic solutions were combined and extracted three times with 10 % hydrochloric acid. The extracts were washed with ethyl acetate, cooled to 0°C, made alkaline with 50 % sodium hydroxide, and extracted three times with ethyl acetate. These extracts were dried over anhydrous sodium sulfate and evaporated to afford 2-methyl-3-[γ-(4-phenylpiperazino)propyl]indole as an oil which solidified by treating with benzene. Recrystallization from benzene gave needles, melting point 130.5°–131.5°C.

By a method similar to the above method, the following compounds were obtained.

3-[γ-(4-Phenylpiperazino)propyl]indole, melting point 125.0°–127.0°C.

3-[γ-(4-o-Methoxyphenylpiperazino)propyl]indole, melting point 157.0°–158.5°C.

3-[γ-(4-o-Tolylpiperazino)propyl]indole, melting point 101.5°–103.0°C

3-[γ-(4-o-Chlorophenylpiperazino)propyl]indole, melting point 141.0°–142.0°C

3-[γ-(4-Benzylpiperazino)propyl]indole, melting point 91.0°–93.0°C.

EXAMPLE 3

Into a solution of 7.2 g of 2-methyl-3-[γ-(4-phenylpiperazino)propyl]-5-fluoroindole in 70 ml of acetic acid was bubbled oxygen containing 3–5 % of ozone at a temperature of 15°–20°C. While bubbling was continued for 90 minutes, the reaction mixture became dark red and then gradually discolored. After the reaction mixture was made alkaline by addition of 10 % sodium hydroxide, it was extracted with chloroform. The extract was washed with water and evaporated to dryness. The residual oil was crystallized by treating with aqueous ethanol to give γ-(4-phenylpiperazino)-2-acetylamino-5-fluorobutyrophenone.

The above-obtained product was treated with anhydrous hydrogen chloride in ether to give crystalline powder of the hydrochloride, melting point 196.5°–198.5°C (decomposition).

EXAMPLE 4

A solution of 3.5 g of γ-(4-phenylpiperazino)-2-acetylamino-5-fluorobutyrophenone and 10 ml of concentrated hydrochloric acid in 70 ml of ethanol was heated under reflux for 4 hours. After ethanol was evaporated under reduced pressure, the reaction mixture was diluted with 100 ml of water, made alkaline with 50 % aqueous sodium hydroxide, and the whole was extracted with ethyl acetate. The extract was washed with water and evaporated to a residue, which was crystallized from aqueous ethanol to yield γ-(4-phenylpiperazino)-2-amino-5-fluorobutyrophenone, melting point 96.0°–98.0°C.

By the method similar to that of the above Examples 3 or 4, the following compounds were obtained.

γ-(4-o-Methoxyphenylpiperazino)-2-acetylamino-4-fluorobutyrophenone hydrochloride hydrate, melting point 181°C (decomposition)

γ-(4-o-Methoxyphenylpiperazino)-2-amino-4-fluorobutyrophenone, melting point 100°C γ-(4-o-Methoxyphenylpiperazino)-2-acetylamino-5-fluorobutyrophenone γ-(4-o-Methoxyphenylpiperazino)-2-amino-5-fluorobutyrophenone.

EXAMPLE 5

To a cooled solution of 3.4 g of γ-(4-phenylpiperazino)-2-amino-4-fluorobutyrophenone in 100 ml of 1N hydrochloric acid was added dropwise 0.7 g of sodium nitrite dissolved in 10 ml of water under stirring at a temperature below 0°C. The resulting diazonium salt solution was added to a cooled solution of 20 ml of 50 % hypophosphorous acid with vigorous stirring. The stirring was continued for 90 minutes below 0°C and the reaction mixture was stored in a refrigerator overnight. The cold reaction mixture was made alkaline with 10 % sodium hydroxide and extracted with ether. The ethereal layer was washed with water, dried over anhydrous sodium sulfate and concentrated to an oily residue, which was crystallized on standing. Recrystallization from isopropanol gave γ-(4-phenylpiperazino)-4-fluorobutyrophenone, melting point 104.0°–106.0°C.

By the method similar to the above method, the following compounds were obtained.

γ-(4-Phenylpiperazino)butyrophenone, melting point 88.5°–90°C

γ-(4-Phenylpiperazino)-4-chlorobutyrophenone, melting point 113.5°–114.5°C

γ-(4-p-Chlorophenylpiperazino)-4-fluorobutyrophenone, melting point 96°–98°C

γ-(4-o-Methoxyphenylpiperazino)-4-fluorobutyrophenone, melting point 73.5°–74.5°C γ-(4-p-Methoxyphenylpiperazino)-4-fluorobutyrophenone, melting point 104.5°–105.5°C γ-(4-p-Methoxyphenylpiperazino)-4-chlorobutyrophenone, melting point 125.5°–127.0°C γ-(4-p-Tolylpiperazino)-4-fluorobutyrophenone, melting point 98°–100°C γ-(4-Phenylpiperazino)-3-fluorobutyrophenone, melting point 73.0°–74.0°C γ-(4-o-Methoxyphenylpiperazino)-3-fluorobutyrophenone, melting point 66.5°–67.5°C

EXAMPLE 6

To a cooled solution of 3.4 g of γ-(4-p-methoxybenzylpiperazino)-2-aminobutyrophenone in 150 ml of 1N hydrochloric acid was added dropwise a solution of 0.7 g of sodium nitrite in 10 ml of water under stirring at a temperature below 0°C. The resulting diazonium salt solution was added to a cooled solution of 20 ml of 50 % hypophosphorous acid under vigorous stirring. The resulting mixture was stirred for additional 2 hours below 0°C and stored in a refrigerator overnight. The cold reaction mixture was made alkaline with 10 % sodium hydroxide and the separated oil was extracted with chloroform. The extract was washed with water, dried over anhydrous potassium carbonate and concentrated to dryness. The residual oil was treated with hydrogen chloride in ether-ethanol to yield γ-(p-methoxybenzylpiperazino)butyrophenone hydrochloride having a melting point of 262.0°–263.0°C (decomposition).

By the method similar to the above method, the following compounds were obtained.

γ-(4-Benzylpiperazino)-4-fluorobutyrophenone, melting point 64.0°–65.0°C; its hydrochloride, melting point 245°–246°C (decomposition)

γ-(4-p-Fluorobenzylpiperazino)-4-fluorobutyrophenone hydrochloride, melting point 256°–258°C γ-(4-p-Bromobenzylpiperazino)-4-fluorobutyrophenone hydrochloride, melting point 248.5°–249.5°C (decomposition)

γ-(4-p-Methylbenzylpiperazino)-4-fluorobutyrophenone hydrochloride, melting point 253°C (decomposition)

γ-(4-o-Methoxybenzylpiperazino)-4-fluorobutyrophenone hydrochloride, melting point 235°–237°C γ-(4-p-Methoxybenzylpiperazino)-4-fluorobutyrophenone hydrochloride, melting point 243°–247°C γ-(4-m-Chlorobenzylpiperazino)-4-fluorobutyrophenone hydrochoride, melting point 249.5°–250.5°C γ-(4-p-Chlorobenzylpiperazino)-4-fluorobutyrophenone hydrochloride, melting point 255°–257°C γ-(4-m-Methoxybenzylpiperazino)-4-fluorobutyrophenone hydrochloride, melting point 226.5°–228.5°C γ-(4-p-Methoxyphenethylpiperazino)-4-fluorobutyrophenone hydrochloride, melting point 260°C (decomposition)

γ-(4-Phenethylpiperazino)-4-fluorobutyrophenone hydrochloride, melting point 252.0°–253.0°C γ-(4-p-Trifluoromethylbenzylpiperazino)-4-fluorobutyrophenone hydrochloride, melting point 234°–237°C

What is claimed is:

1. A compound having the name γ-(4-o-methoxyphenylpiperazino)-2-acetylamino-4-fluorobutyrophenone or its non-toxic pharmaceutically acceptable acid addition salt.

2. A compound having the name γ-(4-o-methoxyphenylpiperzino)-2-amino-4-fluorobutyrophenone or its non-toxic pharmaceutically acceptable acid addition salt.

* * * * *